(12) United States Patent
Timmers et al.

(10) Patent No.: US 6,903,107 B1
(45) Date of Patent: Jun. 7, 2005

(54) SERINE PROTEASE INHIBITOR

(75) Inventors: Cornelis Marius Timmers, Berghem (NL); Johannes Bernardus Maria Rewinkel, Oss (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/830,227

(22) PCT Filed: Oct. 19, 1999

(86) PCT No.: PCT/EP99/07928

§ 371 (c)(1),
(2), (4) Date: Jun. 11, 2001

(87) PCT Pub. No.: WO00/24718

PCT Pub. Date: May 4, 2000

(30) Foreign Application Priority Data

Oct. 19, 1998 (EP) .............................. 98203559

(51) Int. Cl.[7] ...................... A61K 31/517; A61K 31/47; C07D 239/72; C07D 217/22; C07D 215/38
(52) U.S. Cl. .................... 514/266.4; 514/248; 514/310; 514/313; 544/235; 544/293; 546/143; 546/159
(58) Field of Search .............................. 514/248, 266.4, 514/310, 313; 544/235, 293; 546/143, 159

(56) References Cited

FOREIGN PATENT DOCUMENTS

| EP | 0 064 294 A | 11/1982 |
| EP | 0 393 926 A | 10/1990 |
| WO | WO 97 38977 A | 10/1997 |
| WO | WO 98 47876 A | 10/1998 |
| WO | 99/47503 | * 9/1999 |

* cited by examiner

*Primary Examiner*—Richard L. Raymond
*Assistant Examiner*—Tamthom N. Truong
(74) *Attorney, Agent, or Firm*—William M. Blackstone

(57) ABSTRACT

A serine protease inhibitor having the formula (I),

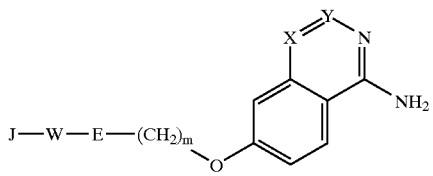

in which

J is H, $R^1$, $R^1$—O—C(O)—, $R^1$—C(O—, $R^1$—$SO_2$—, $R^3OOC$—$(CHR^2)_p$—, $(R^{2a},R^{2b})N$—CO—$(CHR^2)_p$— or Het-CO—$(CHR^2)_p$—;

W is an amino-acid of the formula —NH—$CHR^1$—C(O)—, —$NR^4$—$CH((CH_2)_qC(O)OR^1)$—C(O)—, —$NR^4$—$CH((CH_2)_qC(O)N(R^{2a},R^{2b}))$—C(O)—, —$NR^4$—$CH((CH_2)_qC(O)Het)$-C(O)—, D-1-Tiq, D-3-Tiq, D-Atc, Aic, D-1-Piq, D-3 Piq, glutanyl or a $(C_1$–$C_6)$ alkylester thereof;

E is —$NR^2$—$CH_2$— or the fragment

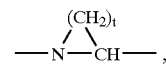

which is unsubstituted or substituted with (1–6C)alkyl, (1–6C)alkoxy or benzyloxy;

$R^1$ is selected form (1–12C)alkyl, (2–12C)alkenyl, (2–12C)alkynyl, (3–12C)cycloalkyl and (3–12C)cycloalkyl(1–6C)alkylene, which groups are unsubstituted or substituted with (3–12C)cycloalkyl, (1–6C)alkoxy, oxo, OH, $CF_3$ or halogen, and from (6–14C)aryl, (7–15C)aralkyl, (8–16C)aralkenyl and (14–20C)(bisary)alkyl, wherein the aryl groups are unsubstituted or substituted with (1–6C)alkyl, (3–12C)cycloalkyl, (1–6C)alkoxy, OH, $CF_3$ or halogen;

$R^2$, $R^{2a}$ and $R^{2b}$ are each independently selected from H, (1–C)alkyl, (3–8C)alkenyl, (3–8C)alkynyl, (3–8C)cycloalkyl and (3–6C)cycloalkyl(1–4C)alkylene, which are unsubstituted or substituted with (3–6C)cycloalkyl, (1–6C)alkoxy, $CF_3$ or halogen, and from (6–14C)aryl and (7–15C)aralkyl, wherein the aryl groups are unsubstituted or substituted with (1–6C)alkyl, (3–6C)cycloalkyl, (1–6C)alkoxy, $CF_3$ or halogen;

$R^3$ is the same as $R^2$ or is Het-(1–6C)alkyl;

$R^4$ is H or (1–3C)alkyl;

X and Y are CH or N, with the proviso that they are not both N;

Het is a 4-, 5- or 6-membered heterocycle containing one or more heteroatoms selected from O, N and S;

m is 1 or 2;

p is 1, 2 or 3;

q is 1, 2 or 3;

t is 2, 3 or 4;

or a pharmaceutically acceptable addition salt or solvate thereof.

10 Claims, No Drawings

SERINE PROTEASE INHIBITOR

The invention relates to a serine protease inhibitor comprising an ether bonded arginine replacement, a pharmaceutical composition containing the same, as well as the use of said serine protease inhibitor for the manufacture of a medicament Serine proteases are enzymes which play an important role in the blood coagulation cascade. Apart from thrombin and factor Xa, other examples of this group of proteases comprise the factors VIIa, IXa, XIa, XIIa, and protein C. Thrombin is the final serine protease enzyme in the coagulation cascade. The prime function of thrombin is the cleavage of fibrinogen to generate fibrin monomers, which are cross-linked to form an insoluble gel. In addition, thrombin regulates its own production by activation of factors V and VII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation. Since inhibitors of thrombin may have a wide range of therapeutic applications, there is a continuous effort to find new serine protease inhibitors. The difficulty in this endeavour is to find a compound in which the properties of therapeutic safety, selectivity, potency and synthetic accessibility are combined. In particular the bioavailability with the oral route of administration can be problematic for selective thrombin inhibitors. In WO 97/16444 thrombine inhibitors are described with modifications of the tripeptide sequence phenylalanyl-prolyl-arginine, in which a carboxyl group is present at the amino terminal and arginine is replaced by a basic (aminoiminomethyl)phenyl or a basic (aminoiminomethyl)pyridinyl group linked to a prolyl analogue by an ether bond.

It is the object of this invention to provide new chemically accessible serine protease inhibitors with a favourable pharmacological and toxicological profile with sufficient potency for therapeutic use.

It has been found that this object can be met with a serine protease inhibitor, and in particular a thrombin inhibitor, having the formula (I), Formula (I)

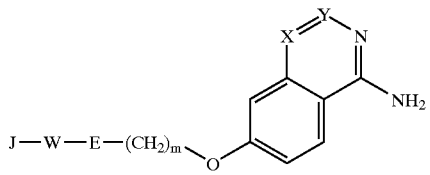

in which

J is H, $R^1$, $R^1$—O—C(O)—, $R^1$—C(O)—, $R^1$—SO$_2$—, $R^3$OOC—(CHR$^2$)$_p$—. ($R^{2a}$,$R^{2b}$)N—CO—(CHR$^2$)$_p$—or Het-CO—(CHR$^2$)$_p$—;

W is an amino-acid of the formula —NH—CHR$^1$—C(O)—, —NR$^4$—CH[(CH$_2$)$_q$C(O)OR$^1$]—C(O)—, —NR$^4$—CH[(CH$_2$)$_q$C(O)N(R$^{2a}$,R$^{2b}$)]—C(O)—, —NR$^4$—CH[(CH$_2$)$_q$ C(O)Het]C(O)—, D-1-Tiq, D-3Tiq, D-Atc, Aic, D-1-Piq or D-3Piq;

E is —NR$^2$—CH$_2$— or the fragment

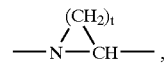

optionally substituted with (1–6C)alkyl, (1–6C)alkoxy or benzyloxy;

$R^1$ is selected from (1–12C)alkyl, (2–12C)alkenyl, (2–12C)alkynyl, (3–12C)cycloalkyl and (3–12C)cycloalkyl (1–6C)alkylene, which groups may optionally be substituted with (3–12C)cycloalkyl, (1–6C)alkoxy, oxo, OH, CF$_3$ or halogen, and from (6–14C)aryl, (7–15C)aralkyl, (8–16C) aralkenyl and (14–20C)(bisaryl)alkyl, whereby the aryl groups may optionally be substituted with (1–6C)alkyl, (3–12C)cycloalkyl, (1–6C)alkoxy, OH, CF$_3$ or halogen;

$R^2$, $R^{2a}$ and $R^{2b}$ are each independently selected from H, (1–8C)alkyl, (2–8C)alkenyl, (2–8C)alkynyl, (3–8C)cycloalkyl and (3–6C)cycloalkyl(1–4C)alkylene, which can each be optionally substituted with (3–8C)cycloalkyl, (1–6C)alkoxy, CF$_3$ or halogen, and from (6–14C)aryl and (7–15C)aralkyl whereby the aryl groups may optionally be substituted with (1–6C)alkyl, (3–6C)cycloalkyl, (1–6C)alkoxy, CF$_3$ or halogen:

$R^3$ is as defined for $R^2$ or Het-(1–6C)alkyl;

$R^4$ is H or (1–3C)alkyl;

X and Y are CH or N with the proviso that they are not both N;

Het is a 4-, 5- or 6-membered heterocycle containing one or more heteroatoms selected from O, N and S;

m is 1 or 2;

p is 1, 2 or 3;

q is 1, 2 or 3;

t is 2, 3 or 4;

and prodrugs thereof, and pharmaceutically acceptable addition salts and/or solvates thereof.

In particular, the compounds of the invention may possess improved bioavailability after oral administration.

In preferred embodiments of this invention compounds have formula (I) in which

J is H, $R^1$, $R^1$—SO$_2$—, $R^3$OOC—(CHR$^2$)$_p$—, ($R^{2a}$,$R^{2b}$) N—CO—(CHR$^2$)$_p$— or Het-CO—(CHR$^2$)$_p$—; more preferred is (3–12C)cycloalkyl optionally substituted with (1–6C)alkoxy; or w is an amino-acid of the formula —NH—CHR$^1$—C(O)—, —NR$^4$—CH[(CH$_2$)$_q$C(O)OR$^1$]—C(O)—. —NR$^4$—CH[(CH$_2$)$_q$C(O)N(R$^{2a}$,R$^{2b}$)]—C(O)—, —NR$^4$—CH[(CH$_2$)$_q$ C(O)Het]—C(O)—; more preferred are an amino acid of the formula —NH—CHR$^1$—C(O)— or an L-amino acid of the formula —NR$^4$—CH[(CH$_2$)$_2$C(O)N(R$^{2a}$,R$^{2b}$)]—C(O)—; or E is —N(3–6C)cycloalkyl-CH$_2$— or the fragment

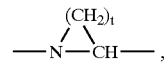

optionally substituted with (1–6C)alkyl, (1–6C)alkoxy or benzyloxy; more preferred is without substitution; or $R^1$ is selected from (1–12C)alkyl, (3–12C)cycloalkyl and (3–12C)cycloalkyl(1–6C)alkylene, which groups may optionally be substituted with (3–12C)cycloalkyl, (1–6C) alkoxy, or oxo and from (6–14C)aryl, (7–15C)aralkyl and (14–20C)(bisaryl)alkyl, whereby the aryl groups may optionally be substituted with (1–6C)alkyl, (3–12C) cycloalkyl, (1–6C)alkoxy, OH, CF$_3$ or halogen; more preferred is a selection from (3–12C)cycloalkyl and (3–12C)

cycloalkyl(1–6C)alkylene, which groups may optionally be substituted with (3–12C)cycloalkyl or (1–6C)alkoxy, and from (6–14C)aryl, (7–15C)aralkyl and (14–20C)(bisaryl) alkyl, whereby the aryl groups may optionally be substituted with (1–6C)alkyl, (3–12C)cycloalkyl, (1–6C)alkoxy or halogen; or $R^2$ is H; or $R^{2a}$ and $R^{2b}$ are each independently selected from H, (1–8C)alkyl, (3–8C)cycloalkyl and (3–6C)cycloalkyl(1–4C) alkylene, which can each be optionally substituted with (3–6C)cycloalkyl or (1–6C)alkoxy, and from (6–14C)aryl and (7–15C)aralkyl whereby the aryl groups may optionally be substituted with (1–6C)alkyl, (3–6C)cycloalkyl, (1–6C) alkoxy, $CF_3$ or halogen; or $R^3$ is selected from H, (1–8C)alkyl, (3–8C)cycloalkyl and (3–6C)cycloalkyl(1–4C)alkylene, which can each be optionally substituted with (3–6C)cycloalkyl or (1–6C)alkoxy, and from (7–15C)aralkyl whereby the aryl groups may optionally be substituted with (1–6C)alkyl, (3–6C)cycloalkyl, (1–6C)alkoxy, $CF_3$ or halogen and from Het-(1–6C)alkyl; more preferred is a selection from (1–8C)alkyl and (3–8C) cycloalkyl, which can each be optionally substituted with (3–6C)cycloalkyl or (1–6C)alkoxy, and from (7–15C) aralkyl whereby the aryl groups may optionally be substituted with (1–6C)alkyl, (3–6C)cycloalkyl, (1–6C)alkoxy, $CF_3$ or halogen and from Het-(1–6C)alkyl; or $R^4$ is H or (1–3C)alkyl; or X and Y are CH; or Het is a 4-, 5- or 6-membered heterocycle containing one or more heteroatoms selected from O, N and S; or m is 2; or p is 1; or q is 2; or t is 3 or 4; more preferred is 4.

In further preferred embodiments W is an amino-acid of the formula —NH—CHR$^1$—C(O)—, or glutamyl [or an (1–6C)alkylester thereof]:

$R^1$ is selected from (3–12C)cycloalkyl and (3–12C) cycloalkyl(1–6C)alkylene, which groups may optionally be substituted with (3–12C)cycloalkyl or (1–6C)alkoxy, and from (6–14C)aryl, (7–15C)aralkyl and (14–20C)(bisaryl) alkyl, whereby the aryl groups may optionally be substituted with (1–6C)alkyl, (3–12C)cycloalkyl, (1–6C)alkoxy or halogen; and $R^3$ is selected from (1–8C)alkyl and (3–8C) cycloalkyl, which can each be optionally substituted with (3–6C)cycloalkyl or (1–6C)alkoxy, and from (7–15C) aralkyl whereby the aryl groups may optionally be substituted with (1–6C)alkyl, (3–5C)cycloalkyl, (1–6C)alkoxy, $CF_3$ or halogen and from Het-(1–6C)alkyl.

Particularly preferred are compounds wherein J is —CH$_2$COO(1–6C)alkyl, (3–8C)cycloalkyl, —SO$_2$-10-camphor, —CH$_2$CONHphenyl or —CH$_2$CONH(3–8C) cycloalkyl. Other highly preferred compounds are those wherein W is D-cyclohexylalaninyl, D-phenylalaninyl, D-diphenylalaninyl or glutamyl [or an (1–6C)alkylester thereof. Also particularly preferred are compounds wherein E is the fragment

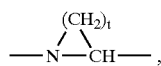

wherein t is 3 or 4.

Herein the terms have the following meaning:

(1–12C)alkyl, (1–8C)alkyl, (1–6C)alkyl, (1–3C)alkyl means a branched or unbranched alkyl group having 1–12, 1–8, 1–6 and 1–3 carbon atoms, respectively, for example methyl, ethyl, propyl, isopropyl, butyl, sec-butyl, tert-butyl, hexyl, octyl and the like.

(2–12C)alkenyl and (2–8C)alkenyl means a branched or unbranched alkenyl group having 2–12, and 2–8 carbon atoms, respectively, such as ethenyl, 2-butenyl, etc.

(2–12C)alkynyl and (2–8C)alkynyl means a branched or unbranched alkynyl group having 2–12 and 2–8 carbon atoms, respectively, such as ethynyl, propynyl, etc.

(1–6C)alkoxy means an alkoxy group having 1–6 carbon atoms, the alkyl moiety having the meaning as previously defined.

(3–12C)cycloalkyl, (3–8C)cycloalkyl, (3–6C)cycloalkyl means a mono- or bicycloalkyl group having 3–12, 3–8 and 3–6 carbon atoms, respectively, like cyclopropyl, cyclobutyl, cyclopentyl, cyclohexyl, cycloheptyl, cyclo-octyl, etc.

(1–6C)alkylene, (1–4C)alkylene means a branched or unbranched alkylene group having 1–6 and 14 carbon atoms, respectively, examples are —(CH$_2$)$_2$— (wherein a corresponds to the number of carbon atoms) —CH(CH$_3$)— and —CH(CH$_3$)—CH$_2$—, etc.

(2–10C)alkenylene means a branched or unbranched alkenylene group having 2–10 carbon atoms and one or more double bonds, like —CH=CH—CH$_2$—, —(CH$_2$)$_2$—CH=CH—CH(CH$_3$)—, —CH=CH—CH=CH—CH$_2$—, etc.

(6–14C)aryl, (6–12C)aryl means an aromatic hydrocarbon group having 6 to 14 or 6–12 carbon atoms, respectively, such as phenyl, naphthyl, tetrahydronaphthyl, indenyl, etc.

(7–15C)aralkyl means an aralkyl group having 7 to 15 carbon atoms, wherein "alkyl" represents a (1–8C)alkylene group and the aryl group is a (6–14C)aryl, both as previously defined.

(8–16C)aralkenyl means an aralkyl group having 8 to 16 carbon atoms, wherein "alkenyl" represents is a (2–10C) alkenylene group and the aryl group is a (6–14C)aryl, both as previously defined.

(14–20C)(bisaryl)alkyl means a (1–3C)alkyl group substituted at the same carbon atom or at different carbon atoms with two independently chosen aryl groups according to the definition of the term (6–12C)aryl, such as the bisphenylmethyl group.

Halogen means F, Cl, Br or I.

Tiq means 1,2,3,4-tetrahydroisoquinoline-3-carboxylic acid.

Atc means 2-aminotetraline-2-carboxylic acid.

Aic means 2-aminoindan-2-carboxylic acid.

Piq means perhydroisoquinolyl carboxylic acid.

The term prodrug means a compound, which after administration is metabolized into one or more active compounds having formula I. Suitable prodrugs are for example N-alkoxycarbonyl protected (preferably N-ethoxycarbonyl) derivatives of the compounds of formula I.

Since the amino-group in aminoisoquinoline, aminoquinazoline or aminophthalazine is having less basicity than amino groups in lysine and arginine, it is unexpected that the newly invented compounds have sufficient efficacy for serine protease inhibition.

As mentioned, amongst the compounds of the present invention are inhibitors of serine proteases involved in the blood coagulation cascade, and in particular inhibitors of thrombin and/or factor Xa. These compounds can be used in medical and veterinary therapy, i.e. for treating and preventing thrombin-mediated and thrombin-associated diseases. This includes a number of thrombotic and prothrombotic states in which the coagulation cascade is activated. Such diseases and states are or occur with, for example, deep vein thrombosis, pulmonary embolism, thrombophlebits, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, certain types of cancer and metastasis, and certain types of neurodegenerative diseases. Compounds of the invention may also be used as in vitro anticoagulants or as anticoagulants in extracorporeal blood circuits, such as those necessary in dialysis and surgery.

According to a further aspect, the present invention provides a method of treating and/or preventing thrombin-mediated and thrombin-associated diseases in an animal or human, which comprises treating said animal or human with a therapeutically effective amount of a compound according to this invention.

The compounds of the invention may be administered enterally (e.g. orally, rectal nasal or topically) or parenterally (e.g. via intramuscular, subcutaneous, intravenous or intraperitoneal injections).

The exact dose and regimen of these compounds and compositions thereof will necessarily depend on the needs of the individual subject to whom a compound of this invention is being administered in the form of a medicament and on the degree of affliction or need and the judgment of the medical practitioner. In general, parenteral administration requires lower dosages than other methods of administration which are more dependent upon absorption. However, the daily dosages are for humans preferably 0.001–100 mg per kg body weight, more preferably 0.01–10 mg per kg body weight.

A daily dose can be administered in one or more dosage units suitable for example for the oral, the rectal, the sublingual or the nasal route or through the skin (for example, transdermal patches, or in the form of a cream).

Another route of administration of a compound of this invention is the introduction thereof into a (dialysis) circuit by other means, e.g. by injecting it either gradually or at once into the system upstream of the dialysis membrane simultaneously with the introduction of the blood into the circuit. Moreover, the lines and/or further equipment of the extracorporeal circuit can be furnished with a compound of this invention, preferably by way of a coating (but not limited to this). Alternatively, a compound of this invention may be adsorbed in the materials of parts of the equipment, e.g. in the membranes used for dialysis.

The invention includes a pharmaceutical composition for inhibiting loss of blood platelet aggregates, inhibiting formation of fibrin, inhibiting thrombus formation, and inhibiting embolus formation in a mammal, comprising a compound of the invention with suitable auxiliaries. These compositions may optionally include anticoagulants, antiplatelets agents, and thrombolytic agents. The pharmaceutical compositions can be added to blood, blood products, or mammalian organs in order to effect the desired inhibitions. The invention also includes a pharmaceutical composition for preventing or treating unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels, in a mammal, comprising a compound of the invention in a pharmaceutical composition. These pharmaceutical compositions may optionally include anticoagulants, antiplatelet agents, and thrombolytic agents. The invention also includes a method for reducing the thrombogenicity of a surface in a mammal by attaching to the surface, either covalently or noncovalently, a compound of the invention.

The invention further includes a pharmaceutical composition, as hereinbefore described, in combination with packaging material suitable for said composition, said packaging material including instructions for the use of the composition as hereinbefore described.

For making means of dosing, such as pills, tablets, suppositories, (micro-)capsules, powders, emulsions, creams, ointments, implants, sprays, injection preparations in the form of a solution or suspension, suitable auxiliaries such as carriers, fillers, binders, lubricants, dispersants, emulsifiers, stabilizers, surfactants, anti-oxidants, colorants, preservatives and the like can be used e.g. as described in the standard reference, Gennaro et al., Remington's Pharmaceutical Sciences, (18th ed., Mack Publishing Company, 1990, see especially Part 8: Pharmaceutical Preparations and Their Manufacture). In general any pharmaceutically acceptable auxiliary which does not interfere with the function of the active compounds is suitable and can be used.

Suitable carriers and fillers with which the active agent of the invention can be administered include for example, agar, alcohol, cellulose derivatives, fats, polysaccharides, polyvinylpyrrolidone, silica, sterile saline, and the like.

Binders are agents used to impart cohesive properties to a pharmaceutical composition resulting in minimal loss from the pharmaceutical composition during production and handling. Binders are for example cellulose, starches, polyvinylpyrrolidone, and the like.

A suitable lubricant with which the active agent of the invention can be administered is, for example, magnesium stearate.

Surfactants are agents facilitating the contact and migration of compounds in different physical environments such as hydrophilic and hydrophobic environments. Many surfactants are known in the art of making pharmaceutical compositions as for example described in chapter 19 of Remington's Pharmaceutical Sciences (18th edition Editor A. R. Gennaro; Mack Publishing Comp; Easton, Pa.). Surfactants that can be used during the process of preparing the pharmaceutical formulation are, for example, polyethylene glycol (PEG), and the like.

The compounds may also be used with implantable pharmaceutical devices such as those described in U.S. Pat. No. 4,767,628, the contents of which are incorporated by this reference. Then the device will contain sufficient amounts of compound to slowly release the compound (e.g. for more than a month).

Compounds of formula (I) may be prepared from a compound of formula (II), or derivatives thereof wherein the amino group at the aromatic group (arylamino) is protected as urethane such as Alloc or amide such as benzoyl, wherein W, E, X, Y and m have the previously defined meaning and Pg is an N-protecting group (preferably urethane such as Boc).

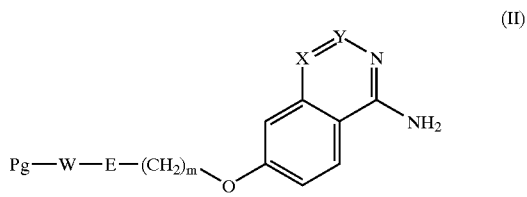

The term N-protecting group as used in this document means a group commonly used in peptide chemistry for the protection of an a-amino group, like the allyloxycarbonyl (Alloc) group, the tert-butyloxycarbonyl (Boc) group, the benzyloxycarbonyl (Z) group, the 9-fluorenylmethyloxycarbonyl (Fmoc) group or the phthaloyl (Phth) group. Removal of the protecting groups can take place in different ways, depending on the nature of those protecting groups. An overview of amino protecting groups and methods for their removal is given in the above mentioned The Peptides, Analysis, Synthesis, Biology, Vol 3. and in T. W. Greene and P. G. M. Wuts, Protective Groups in Organic Synthesis, 2nd edition, 1991, John Wiley & Sons, Inc. .

Removal of the N-protecting group Pg and optional modification(s) of the deprotected amine group using methods known in the field such as peptide coupling, alkylation or reductive amination give compounds of formula (I). Compounds of formula (II) can be prepared from a compound of formula (III), or derivatives thereof wherein the arylamino is protected as urethane such as Alloc or amide such as benzoyl, wherein E, X, Y, m and Pg have the previously defined meanings. Removal of the N-protecting group Pg in compounds of formula (III) and peptide coupling with compounds of formula Pg-w-OH, in which W and Pg have the previously defined meaning, yields compounds of formula (II).

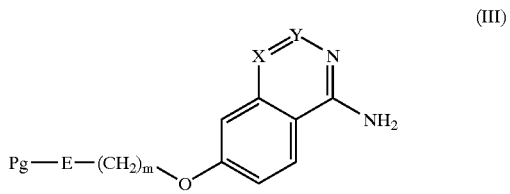

(III)

Alternatively, compounds of formula (I) can be prepared directly from compounds of formula (III). Removal of the N-protecting group Pg in compounds of formula (III) and a peptide coupling with a compounds of formula J-W-OH, in which J and W have the previously defined meanings and may optionally contain a additional protecting group, afford compounds of formula (I). Compounds of formulas (I), (II) and (III) are accessible from those of formula (IV) wherein X and Y have the previously defined meanings, or derivatives thereof wherein the arylamino is protected as urethane such as Alloc or amide such as benzoyl, by reaction with alcohols of formula J-W-E-$(CH_2)_m$—OH, Pg-W-E-$(CH_2)_m$—OH or Pg-E-$(CH_2)_m$—OH, in which W, E, J, m and Pg have the previously defined meanings and optionally containing a protecting group, under standard Mitsunobu conditions (tributhylphosphine, dialkyl azodicarboxylate) (R. L. Elliot, H. Kopecka, D. E. Gunn, H.-N. Lin and D. S. Garvey, Biorgs. Med. Chem. Lett., 6, 2283 (1996); K. Wisniewski, A. S. Koldziejczyk and B. Falkiewicz, J. Pept. Sc., 4, 1 (1998)).

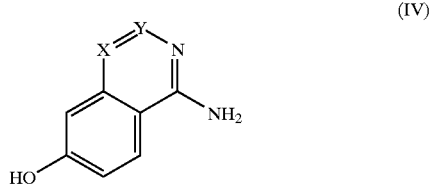

(IV)

Alcohols of type formula Pg-E-$(CH_2)_m$—OH in which E=—$R^3NCH_2$— and m=2 are accessible by conjugate addition of the corresponding amine $R^3NH_2$ to ethyl acrylate, reduction of the ester function with lithium aluminium hydride, and subsequent introduction of the N-protecting group Pg.

Demethylation of methyl aryl ethers of formula (V) to the corresponding phenolic compounds of formula (IV) may be accomplished by reaction with $BBr_3$ [J. F. W. McOmie and D. E. West, Org. Synth., Collect. Vol. V, 412 (1973)] or EtSNa [A. S. Kende and J. P. Rizzi, Tetrahedron Lett., 22, 1779 (1981)].

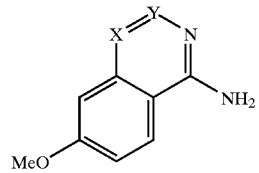

(V)

Suitable starting material to prepare compounds of formula (V) are compounds of formula (VI) wherein X and Y have the previously defined meanings. The chloro group of compounds of formula (VI) can be transformed directly into an amine group by heating the former with ammonia under pressure. Alternatively, the chloro group of compounds of formula (VI) can be converted into a phenoxy group by reaction with phenol under alkaline conditions, and subsequently treatment with ammonium acetate affords the amine group of compounds of formula (V). Compounds of formula (V) can also be obtained by treatment of compounds of formula (VI) with sodium azide and subsequent reduction of the aryl azide with $PPh_3$.

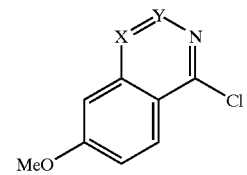

(VI)

Compounds of formula (VI) wherein X and Y have the previously defined meanings can be obtained from compounds of formula (VII) by treatment with phosphoryl chloride. Compounds of formula (VII) are described in literature; 7-methoxy-3H-quinazolin-4-one: Chapman et al., J. Chem. Soc. 890 (1947), 6-methoxy-2H-phthalazin-1-one: Consonni P. and A. Omodei-Sale, Farmaco, Ed.Sci. 76, 691 (1976) (Chem. Abstr. 85-177191). The compound of formula (VI) wherein X=CH and Y=CH (1-chloro-6-methoxy-isoquinoline) can be prepared by converting 6methoxy-isoquinoline (Hendrickson, J. B.; Rodriguez, C.; J. Org. Chem. 1983, 48, 3344–3346) into the N-oxide salt, e.g. with a peracid, such as m-chloroperbenzoic acid, followed by HCl treatment, and subsequently reacting this N-oxide salt with a chlorinating reagent, like phosphoryl chloride (J. Robinson, J. Am. Chem. Soc., 69, 1941 (1939)).

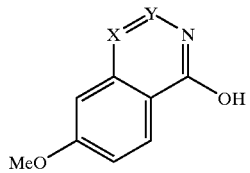

(VII)

The peptide coupling, as mentioned as a procedural step in the above described method to prepare the compounds of the invention, can be carried out by methods commonly known in the art for the coupling—or condensation—of peptide fragments such as by the azide method, mixed anhydride method, activated ester method, or, preferably, by the carbodiimide method, especially with the addition of catalytic and racemisation suppressing compounds like N-hydroxysuccinimide and N-hydroxybenzotriazole. Suitable methods are described in: The Peptides, Analysis, Synthesis, Biology, Vol 3, E. Gross and J. Meienhofer, eds. (Academic Press, New York, 1981), R. Knorr, A. Trzeciak, W. Bannwarth and D. Gillessen, *Tetrahedron Lett.*, 30, 1927 (1989) and L. A. Carpino, *J. Am. Chem. Soc.*, 115, 4397 (1993).

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The invention is illustrated by the following examples.

EXAMPLES

The following abbreviations are used:

Alloc: allyloxycarbonyl
Boc: tert-butoxycarbonyl
eluent: x-y% solvent A in solvent B means that a gradient of the eluent of x% (v/v) of solvent A in solvent B to y% (v/v) of solvent A in solvent B was used.

Example 1

(2S)-1-(N-(-)-camphorsulphonyl-D-cyclohexylalaninyl)-2-(2-(1-amino-isoquinolin-6-oxy)-eythyl)-piperidine 1a. 6-Methoxy-isoquinoline-N-oxide hydrochloride At room temperature 133 g of m-chloroperbenzoic acid (purity 75%) was added in portions to a stirred solution of 6-methoxy-isoquinoline [Hendrickson, J. B.; Rodriguez, C.; J. Org. Chem. 1983, 48, 3344–3346; 79.8 g; 500 mmol] in 1.2 L of dichloromethane. Stirring was continued for 3 hours and subsequently methanol (1 L) was added. The bulk was reduced to 700 mL after which 800 mL of a saturated solution of hydrogen chloride in diethyl ether was added. Dilution with 1.5 L of diethyl ether resulted in precipitation of yellow crystals, which were separated by filtration, washed with chilled diethyl ether and dried in vacuo. Yield: 85 g (80%); white solid; m.p. 189–191° C.; (+)-FAB-MS: 176 (MH$^+$-HCl).

1b. 1-Chloro-6methoxy-isoquinoline

6-Methoxy-isoquinoline-N-oxide hydrochloride (1a, 85 g; 400 mmol) was carefully added in portions to phosphoryl chloride (550 mL) at a temperature of 90° C., after which the mixture was stirred for 6 h at 90° C. Excess of phosphoryl chloride was removed in vacuo. The remaining white solid was washed with water, filtered and dried in vacua. Yield: 68 g (88%); white solid; m.p. 72–74° C.; El-MS: 193 (M$^+$).

1c. 6-Methoxy-1l-phenoxy-isoquinoline

To a mixture of 1-chloro-6methoxy-isoquinoline (1b, 16.8 g, 87 mmol) and phenol (67 g) was added powdered potassium hydroxide (8.4 g). The mixture was heated under a nitrogen atmosphere to 140° C. for 3 h, allowed to cool to room temperature and subsequently diluted with 280 mL of 3 N sodium hydroxide solution and 500 mL of dichloromethane. The organic layer was washed with 2 N sodium hydroxide, water and brine, dried over magnesium sulphate and concentrated under reduced pressure, yielding 21.3 g (98%) of a white solid. ESI-MS: 251.8 (M+H)$^+$. Rf (silica gel; toluene/ethanol, 8/2, v/v): 0.75.

1d. 1-Amino-6methoxy-isoquinoline

A mixture of 6-methoxy-1-phenoxy-isoquinoline (1c, 21.3 g, 85 mmol) and ammonium acetate (55 g) was heated, under a nitrogen atmosphere, to 150° C. and stirred overnight. The mixture was allowed to cool to room temperature, after which 3 N sodium hydroxide solution (280 mL) was added under stirring. The thus obtained solution was extracted with ethyl acetate (2×300 mL) and the combined organic layers were extracted with 2 N hydrochloric acid (100 mL), containing brine. Subsequently, the pH of the aqueous layer was adjusted to 12 with 2 N sodium hydroxide solution. Extraction with ethyl acetate (300 mL) then afforded an organic layer, which was washed with brine (100 mL), dried (magnesium sulphate) and concentrated under reduced pressure, furnishing 11 g of a white solid (75%). ESI-MS: 175.2 (M+H)$^+$, 349.2 (M+2H)$^{2+}$. Rf (silica gel; toluene/ethanol, 8/2, v/v): 0.17.

1e. 1-Amino-6-hydroxy-isoquinoline

A solution of boron tribromide (18.2 mL; 370 mmol) in 20 mL of dichloromethane was added dropwise to a stirred solution of 1-amino-6methoxy-isoquinoline (1d, 11.0 g; 63 mmol) in 150 mL of dichloromethane at 10° C. After stirring for 4 d at ambient temperature the reaction mixture was poured into ice and the pH was adjusted to 9 by adding concentrated aqueous ammonia. The precipitated material was collected by filtration and dried in vacuo to give 8.9 g (88%) of the title compound as a white solid; m.p. 258–260° C.; El-MS: 160 (M$^+$). $^1$H NMR (DMSO-d6): δ 8.11 (d, 1H), 7.65 (d, 1H), 6.99 (dd, 1H), 6.86 (d, 1H), 6.80–6.63 (m, 4H), 5.2 (bs, 1H).

1f. (2S)-1-tert-butoxycarbonyl-2-(2-(1-amino-isoquinolin-6-oxy)-ethyl)-piperidine (2S)-1-tert-Butoxycarbonyl-2-(2-hydroxyethyl)-piperidine [Ikeda, M.; Kugo, Y.; Sato, T.; *J. Chem. Soc. Perkin Trans.*/11996, 15, 1819–1824; 860 mg, 3.75 mmol], prepared from resolved (2S)-2-(2-hydroxyethyl)-piperidine [Beyerman, H. C.; *Recl. Trav. Chim. Pays-Bas* 1971, 90, 755–765], 1-amino-6-hydroxy-isoquinoline (1e, 480 mg. 3.0 mmol) and tributylphosphine (1.5 ml, 6.0 mmol) were dissolved in tetrahydrofuran/N,N-dimethylformamide (4:1, v/v, 15 mL). Subsequently, a solution of diethyl azodicarboxylate (0.95 ml, 6.0 mmol) in tetrahydrofuran (5 mL) was added dropwise. After stirring overnight, the mixture was diluted with dichloromethane (100 mL), washed with 2 N sodium hydroxide (2×50 mL), dried (magnesium sulphate) and concentrated under reduced pressure. Purification of the residue was accomplished using silica gel chromatography (eluent: 2–10% methanol in dichloromethane), yielding 827 mg (60%) of a white foam. ESI-MS: 372.2 $(M+H)^{30}$. Rf (silica gel; dichloromethane/methanol, 9/1, v/v): 0.41. The same reaction was also carried out with unresolved 1-tert-butoxycarbonyl-2-(2-hydroxyethyl)-piperidine (10 mmol scale, 63% yield).

1g. (2S)-2-(2-(1-allyloxycarbonylamino-isoquinolin-6oxy)-ethyl)-piperidine

To a stirred solution of (2S)-(1-tert-butoxycarbonyl)-2-(2-(1-amino-isoquinolin-6oxy)-ethyl)-piperidine (1f, 371 mg, 1.0 mmol) in pyridine/dichloromethane (1:2, v/v, 5 mL) was added allyl chloroformate (117 μl, 1.1 mmol). After 2 h of stirring, the reaction mixture was quenched by addition of water, concentrated in vacua, redissolved in dichloromethane (50 mL) and washed with a saturated sodium hydrogencarbonate solution (2×25 mL). Drying over magnesium sulphate and concentration under reduced pressure afforded 460 mg (100%) of a colourless oil, which was dissolved in trifluoroacetic acid/dichloromethane (1:1, v/v, 10 mL) and stirred for 2 h. Subsequently, the reaction mixture was concentrated in vacua and subjected to silica gel column chromatography (eluent: 2–12% methanol in dichloromethane), which provided 285 mg (80%) of the title compound as a white foam. ESI-MS: 356.4 $(M+H)^{30}$, 281.4 $(M+H-Alloc)^+$. Rf (silica gel; dichloromethane/methanol, 9/1, v/v): 0.62.

1h. N-(−)-camphorsulphonyl-D-cyclohexylalanine (−)-Camphorsulphonyl chloride (3.0 g, 12 mmol) was added dropwise to a stirred mixture of D-cyclohexylalanine HCl-salt (2.08 g, 10 mmol), 1,4-dioxane (20 mL) and saturated aqueous sodium hydrogencarbonate (10 mL). The heterogeneous mixture was stirred overnight and subsequently carefully acidified (pH=3) using 1 N hydrochloric acid. Extraction of this mixture with dichloromethane (2×100 mL), followed by drying over magnesium sulphate and concentration under reduced pressure furnished 3.22 g (84%) of the title compound as a white solid. ESI-MS: 386.5 $(M+H)^+$, 384.5 $(M-H)^{31}$. Rf (silica gel; dichloromethane/methanol, 9/1, v/v): 0.32.

1i. (2S)-1-(N-(−)-camphorsulphonyl-D-cyclohexylalaninyl)-2-(2-(1-allyloxycarbonyl-amino-isoquinolin-6-oxy)-ethyl)-piperidine 2-(1H-benzotriazol-1-yl)-1,1,3,3-tetramethyluronium tetrafluoroborate (TBTU, 321 mg, 1.0 mmol) was added to a stirred solution of (2S)-1-tert-butoxycarbonyl-2(2-(1-allyloxycarbonylamino-isoquinolin-6-oxy)ethyl)-piperidine (1g, 285 mg, 0.80 mmol), N-(−)-camphorsulphonyl-D-cyclohexylalanine (1h, 308 mg, 0.80 mmol) and N,N-diisopropylethylamine (348 μl, 2.0 mmol) in dichloromethane (5 mL). After stirring overnight, the reaction mixture was diluted with dichloromethane (50 mL), washed with saturated aqueous sodium hydrogencarbonate (25 mL) and 0.1 N hydrochloric acid (25 mL), dried (magnesium sulphate) and concentrated under reduced pressure. Purification of the residue was effected by silica gel chromatography (eluent: 0–5% methanol in dichloromethane), yielding 480 mg (83%) of a white solid. ESI-MS: 723.6 $(M+H)^{30}$. Rf (silica gel; dichloromethane/methanol, 19/1, v/v): 0.34.

1j. (2S)-1-(N-(−)-camphorsulphonyl-D-cyclohexylalaninyl)-2-(2-(1-amino-isoquinolin-6-oxy)ethyl)-piperidine Under a continuous stream of dry nitrogen, tetrakis-(triphenylphosphine) palladium(0) (30 mg, 0.03 mmol) was added to a stirred solution of (2S)-1-(N-(−)-camphorsulphonyl-D-cyclohexylalaninyl)-2-(2-(1-allyloxycarbonylamino-isoquinolin-6-oxy)-ethyl)-piperidine (1i, 480 mg, 0.66 mmol) and morpholine (0.26 ml, 3.0 mmol) in tetrahydrofuran (5 mL). The reaction mixture was stirred for 2 h and subsequently concentrated in vacuo. Residual morpholine was removed by coevaporation with 1,4-dioxane and the mixture was subjected to preparative RP-HPLC (Delta Pak $C_{18}$, 100 Å, 15 μm): Mob. phase: A=0.5 M $NaH_2PO_4+H_3PO_4$ pH 2.1; $B=H_2O$; $C=CH_3CN/H_2O$ (3:2, v/v).

| Gradient: | Time (min) | % A | % B | % C |
|---|---|---|---|---|
| | 0 | 20 | 60 | 20 |
| | 30 | 20 | 20 | 60 |
| | 32 | 20 | 0 | 80 |
| | 37 | 20 | 0 | 80 |
| | 50 | 20 | 60 | 20 |

After collection of the appropriate fractions, the mixture was desalted using 0.1 N. hydrochloric acid and subsequently lyophilized, yielding 227 mg (54%) of the title compound as a white fluffy solid. ESI-MS: 639.6 $(M+H)^+$, 637.6 $(M-H)^-$, 673.4 $(M+Cl)^-$. Anal. HPCL (Supelcosil LC-18-DB 5 um, 250*2.1 mm): Mob. phase: A=0.5 M $NaH_2PO_4+H_3PO_4$ pH 2.1; $B=H_2O$; $C=CH_3CN/H_2O$ (3:2, v/v).

| Gradient: | Time (min) | % A | % B | % C |
|---|---|---|---|---|
| | 0 | 20 | 60 | 20 |
| | 30 | 20 | 0 | 80 |
| | 40 | 0 | 0 | 100 |
| | 50 | 0 | 0 | 100 |

Retention time: 39.27 min (96.0% purity).

Eample 2

N-(N'-propoxylmethyl-D-cyclohexylalaninyl)-N-(3-(1-amino-isoquinolin-6-oxy)-propyl))-cyclohexylamine 2a. Ethyl N-tert-butoxycarbonyl-3-cyclohexylamino-propanoate Ethyl acrylate (1.09 ml, 10 mmol) was added to a stirred solution of cyclohexylamine (1.14 ml, 10 mmol) in ethanol/tetrahydrofuran (1:1, v/v, 30 mL). After stirring overnight, pyridine and di-tert-butyl dicarbonate were subsequently added and the mixture was stirred for an additional 5 h. Concentration of the reaction mixture, followed by purification of the residue by silica gel chromatography (eluent ethyl acetate/heptane, 1:4, v/v) provided 2.18 g (73%) of the title compound as a white foam. ESI-MS: 300.2 $(M+H)^+$, 244.2 $(M+H-C_4H_8)^{30}$, 200.2 $(M+H-Boc)^+$. Rf (silica gel; ethyl acetate, 1:4, v/v): 0.51.

2b. N-tertbutoxycarbonyl-3cyclohexylamino-propanol

To a stirred solution of ethyl N-tert-butoxycarbonyl-3-cyclohexylamino-propanoate (2a, 2.18 9, 7.3 mmol) in tetrahydrofuran (20 mL) was added lithium aluminium hydride (1.0 M solution in tetrahydrofuran. 10 mL). The reaction mixture was stirred for 1 h, after which ethyl acetate (5 mL) was slowly added. Subsequently, aqueous citric acid (0.5 M, 50 mL) was added and the heterogeneous mixture was extracted with Et$_2$O (2×100 mL). The organic layer was washed with aqueous sodium hydrogencarbonate (1 N, 25 mL). Drying over magnesium sulphate, concentration under reduced pressure and purification by silica gel chromatography (eluent: ethyl acetate/heptane, 3:7, v/v) provided 1.50 g (80%) of the title compound as a white foam. ESI-MS: 258.2 (M+H)$^+$, 280.3 (M+Na)$^+$, 202.2 (M+H—C$_4$H$_8$)$^+$, 158.2 (M+H-Boc)$^+$. Rf (silica gel; ethyl acetate/heptane, 1:4, v/v): 0.31.

2c. N-tert-butoxycarbonyl-N-(3-(1-amino-isoquinolin-6-oxy)-propyl))-cyclohexylamine This compound was prepared from N-tert-butoxycarbonyl-3-cyclohexylamino-propanol (2b, 257 mg, 1.0 mmol) and 1-amino-6hydroxy-isoquinoline (1e, 160 mg, 1.0 mmol) by the Mitsunobu procedure described in Example 1f. Yield: 260 mg (65%). ESI-MS: 400.1 (M+H)$^+$, 344.1 (M+H—C$_4$H$_8$)$^+$, 300.1 (M+H-Boc)$^+$. Rf (silica gel; dichloromethane/methanol, 9:1, v/v): 0.28.

2d. N-(3-(1-allyloxycarbonylamino-isoquinolin-6-oxy)-propyl))-cyclohexylamine

The title compound was prepared by Alloc-protection and subsequent Boc-removal of N-tert-butoxycarbonyl-3-(1-amino-isoquinolin-6-oxy)-propyl)-cyclohexylamine (2c, 260 mg, 0.65 mmol) according to the procedure described in Example 1 g. Yield: 177 mg (71%). ESI-MS: 384.2 (M+H)$^+$, 300.2 (M+H-Alloc)$^+$. Rf (silica gel; dichloromethane/methanol, 17:3, v/v): 0.47.

2e. D-cyclohexylalanine benzyl ester hydrochloride

To a stirred solution of N-tert-butoxycarbonyl-D-cyclohexylalanine (2.71 g. 10 mmol) in methanol (50 mL), containing 1 mL of water, was added cesium carbonate (1.63 g, 5.0 mmol). After stirring for 2 h, the reaction mixture was concentrated in vacuo and redissolved in N,N-dimethylformamide (50 mL). Subsequently, benzyl bromide (2.38 ml, 20 mmol) was added and the reaction mixture was stirred overnight. The mixture was diluted with ethyl acetate (200 mL), washed with aqueous sodium hydrogencarbonate (1 M, 2×50 mL), dried (magnesium sulphate) and concentrated under reduced pressure. Purification of the residue was accomplished using silica gel chromatography (eluent 0–30% ethyl acetate in heptane). The combined fractions were concentrated in vacuo and subsequently treated with 3M hydrogen chloride in 1,4-dioxane (50 mL). After stirring overnight, the reaction mixture was concentrated under reduced pressure, yielding 2.94 g (74%) of the title compound as a white foam. ESI-MS: 262.4 (M+H)$^+$. Rf (silica gel; dichloromethane/methanol, 19/1, v/v): 0.41.

2f. N-tert-butoxycarbonyl-N-propoxycarbonylmethyl-D-cyclohexylalanine benzyl ester n-Propyl bromoacetate (1.05 ml, 8.1 mmol) was added to a stirred solution of D-cyclohexylalanine benzyl ester.HCl (2.94 g, 7.4 mmol) and N,N-diisopropylethylamine (3.5 ml, 20 mmol) in acetonitrile (20 mL). The reaction mixture was allowed to stir for 6 d and subsequently concentrated under reduced pressure. The residue was dissolved in dichloromethane (100 mL) and washed with aqueous sodium hydrogencarbonate (1 M, 50 mL), dried (magnesium sulphate) and concentrated in vacuo. The crude substance was redissolved in dichloromethane (20 mL) and subsequently treated with N,N-diisopropylethylamine (3.5 ml, 20 mmol) and di-tert-butyl dicarbonate (1.74 g, 8.0 mmol). After stirring for 4 d, the reaction mixture was concentrated under reduced pressure and purified by silica gel chromatography (eluent: 0–50% ethyl acetate in heptane), yielding 2.39 g (70%) of the title compound as a colourless oil. ESI-MS: 461.5 (M+H)$^+$, 407.5 (M+H—C$_4$H$_8$)$^+$361.5 (M+H-Boc)$^+$. Rf (silica gel; ethyl acetate/heptane, 1/3, v/v): 0.27.

2g. N-tert-butoxycarbonyl-N-propoxycarbonylmethyl-D-cyclohexylalanine

A solution of N-tert-butoxycarbonyl-N-propoxycarbonylmethyl-D-cyclohexylalanine benzyl ester (2f, 2.39 g, 5.2 mmol) in N,N-dimethylformamide (25 mL) was treated with palladium on activated charcoal (10% Pd. 250 mg). Hydrogen gas was bubbled through the latter solution under atmospheric pressure for a period of 2 h. Subsequently, the reaction mixture was filtered over Celite and the filtrate was evaporated under reduced pressure, providing 1.90 g (98%) of the title compound as a white solid. ESI-MS: 371.2 (M+H)$^+$, 369.2 (M−H)$^-$, 315.2 (M+H—C$_4$H$_8$)$^+$271.5 (M+H-Boc)$^+$. Rf (silica gel; dichloromethane/methanol, 9/1, v/v): 0.42.

2h. N-(N'-tert-butoxycarbonyl-N'-propoxycarbonylmethyl-D-cyclohexylalaninyl)-N-(3-(1-allyloxycarbonylamino-isoquinolin-6-oxy)-propyl))-cyclohexylamine This compound was prepared from N-(3-(1-allyloxycarbonylamino-isoquinolin-6-oxy)-propyl))-cyclohexylamine (2d, 192 mg, 0.50 mmol) and N-tert-butoxycarbonyl-N-propoxycarbonylmethyl-D-cyclohexylalanine (2g, 185 mg, 0.50 mmol) by the peptide coupling procedure described in Example 1i. Yield: 221 mg (60%). ESI-MS: 737.6 (M+H)$^+$, 681.5 (M+H—C$_4$H$_8$)$^+$, 637.6 (M+H-Boc)$^+$. Rf (silica gel; dichloromethane/methanol, 9:1, v/v): 0.68.

2i. N-(N'-propoxycarbonylmethyl-D-cyclohexylalaninyl)-N-(3-(1-amino-isoquinolin-6-oxy)-propyl))cyclohexylamine The title compound was prepared from N-(N'-tert-butoxycarbonyl-N'-propoxycarbonylmethyl-D-cyclohexylalaninyl)N-(3-(1-allyloxycarbonylamino-isoquinolin-6-oxy)-propyl))-cyclohexylamine (2h, 221 mg, 0.30 mmol) according to the procedure described in Example 1i for the removal of the allyloxycarbonyl group. Subsequently, the crude product was treated With dichloromethane/trifluoroacetic acid (1:1, v/v, 10 mL) and stirred for 2 h, after which the reaction mixture was concentrated in vacuo. Purification of the residue was effected by the preparative HPLC procedure described in Example 1j. Desalting using 0.1 N hydrochloric acid and subsequent lyophilization yielded 67 mg (41%) of the title compound as a white fluffy solid. ESI-MS: 553.6 (M+H)$^+$, 587.9 (M+Cl). Anal. HPLC retention time (gradient Example 1j): 27.91 min (95.8% purity).

Example 3

N-(N'-propoxycarbonylmethyl-D-cyclohexylalaninyl)-N-(3-(1-amino-isoquinolin-6-oxy)-propyl))-cyclopentylamine 3a. Ethyl N-tertbutoxycarbonyl-3-cyclopentylamino-propanoate The title compound was prepared from ethyl acrylate (1.09 ml, 10 mmol) and cyclopentylamine (0.99 ml, 10 mmol) according to Example 2a. Yield: 2.28 g (80%). ESI-MS: 286.2 (M+H)$^+$, 230.2 (M+H—C$_4$H$_8$)$^+$, 186.2 (M+H-Boc)$^+$. Rf (silica gel; ethyl acetate/heptane, 1:4, v/v): 0.45.

3b. N-tert-butoxycarbonyl-3-cyclopentylamino-propanol

This compound was prepared from N-tert-butoxycarbonyl-3-cyclopentylamino-propanoate (3a, 2.28 g, 8.0 mmol) using the procedure described in Example 2b. Yield: 1.34 g (69%). ESI-MS: 244.2 (M+H)$^+$, 266.3 (M+Na)$^+$, 188.2 (M+H—C$_4$H$_8$)$^+$, 144.2 (M+H-Boc)$^+$. Rf (silica gel; ethyl acetate/heptane, 1:4, v/v): 0.30.

3c. N-tert-butoxycarbonyl-N-(3-(1-amino-isoquinolin-6-oxy)-propyl))-cyclopentylamine This compound was prepared from N-tert-butoxycarbonyl-3-cyclopentylamino-propanol (3b, 243 mg, 1.0 mmol) and 1-amino-6-hydroxy-isoquinoline (1e, 160 mg, 1.0 mmol) by the Mitsunobu procedure described in Example 1f. Yield: 262 mg (68%). ESI-MS: 386.1 (M+H)$^+$, 330.1 (M+H—C$_4$H$_8$)$^+$, 286.1 (M+H-Boc)$^+$. Rt (silica gel; dichloromethane/methanol, 9:1, v/v): 0.25.

3d. N-(3-(1-allyloxycarbonylamino-isoquinolin-6-oxy)-propyl))-cyclopentylamine The title compound was prepared by Alloc-protection and subsequent Boc-removal of N-tert-butoxycarbonyl-3-(1-amino-isoquinolin-6-oxy)-propyl)-cyclopentylamine (3c, 62 mg, 0.68 mmol) according to the procedure described in Example 1g. Yield: 171 mg (68%). ESI-MS: 370.2 (M+H)$^+$, 286.2 (M+H-Alloc)$^+$. Rf (silica gel; dichloromethane/methanol, 17:3, v/v): 0.44.

3e. N-(N'-tert-butoxycarbonyl-N'-propoxycarbonylmethyl-D-cyclohexylalaninyl)-N-(3-(1-allyloxycarbonylamino-isoquinolin-6-oxy)-propyl))-cyclopentylamine This compound was prepared from N-(3-(1-allyloxycarbonylamino-isoquinolin-6-oxy)-propyl))-cyclopentylamine (3d, 185 mg, 0.50 mmol) and N-tert-butoxycarbonyl-N-propoxycarbonylmethyl-D-cyclohexylalanine (2g, 185 mg, 0.50 mmol) by the peptide coupling procedure described in Example 1i. Yield: 256 mg (71%). ESI-MS: 723.6 (M+H)$^+$, 667.5 (M+H—C$_4$H$_8$)$^+$, 623.6 (M+H-Boc)$^+$. Rf (silica gel; dichloromethane/methanol, 9:1, v/v): 0.64.

3f. N-(N'-propoxycarbonylmethyl-D-cyclohexylalaninyl)-N-(3-(1-amino-isoquinolin-6-oxy)propyl))-cyclopentylamine The title compound was prepared from N-(N'-tert-butoxycarbonyl-N'-propoxycarbonylmethyl-D-cyclohexylalaninyl)-N-(3-(1-allyloxycarbonylamino-isoquinolin-6-oxy)propyl))-cyclopentylamine (3e, 256 mg, 0.35 mmol) according to the procedure described in Example 2i for the removal of the Alloc and Boc protective groups. Purification of the residue was effected by the preparative HPLC procedure described in Example 1j. Desalting using 0.1 N hydrochloric acid and subsequent lyophilization yielded 113 mg (59%) of the title compound as a white fluffy solid. ESI-MS: 539.5 (M+H)$^+$, 573.9 (M+Cl). Anal. HPLC retention time (gradient Example 1j): 25.84 min (90.1% purity).

Example 4

N-N'-propoxycarbonylmethyl-D-cyclohexylalaninyl)-N-(3-(1-amino-isoquinolin-6-oxy)-propyl))-cyclobutylamine

4a. Ethyl N-tert-butoxycarbonyl-3-cyclobutylamino-propanoate

The title compound was prepared from ethyl acrylate (1.09 ml, 10 mmol) and cyclobutylamine (0.85 ml, 10 mmol) according to Example 2a. Yield: 1.71 9 (63%). ESI-MS: 272.2 (M+H)$^+$, 216.2 (M+H—C$_4$H$_8$)$^+$, 172.2 (M+H-Boc)$^+$. Rf (silica gel; ethyl acetate/heptane, 1:4, v/v): 0.44.

4b. N-tertbutoxycarbonyl-3-cyclobutylamino-propanol

This compound was prepared from N-tertbutoxycarbonyl-3-cyclobutylamino-propanoate (4a, 1.71 9, 6.3 mmol) using the procedure described in Example 2b. Yield: 0.94 g (65%). ESI-MS: 230.2 (M+H)$^+$. 252.3 (M+Na)$^+$, 174.2 (M+H—C$_4$H$_8$)$^+$. Rf (silica gel; ethyl acetate/heptane, 1:4, v/v): 0.37.

4c. N-tertbutoxycarbonyl-N-(3-(1-amino-isoquinolin-6-oxy)-propyl))-cyclobutylamine This compound was prepared from N-tert-butoxycarbonyl-3-cyclobutylamino-propanol (4b, 229 mg, 1.0 mmol) and 1-amino-6-hydroxy-isoquinoline (1e, 160 mg, 1.0 mmol) by the Mitsunobu procedure described in Example 1f. Yield: 230 mg (62%). ESI-MS: 372.1 (M+H)$^+$, 316.1 (M+H—C$_4$H$_8$)$^+$, 272.1 (M+H-Boc)$^+$. Rf (silica gel; dichloromethane/methanol, 9:1, v/v): 0.26.

4d. N-(3-(1-allyloxycarbonylamino-isoquinolin-6-oxy)-propyl))-cyclobutylamine The title compound was prepared by Alloc-protection and subsequent Boc-removal of N-tert-butoxycarbonyl-3-(1-amino-isoquinolin-6-oxy)-propyl)-cyclobutylamine (4c, 230 mg, 0.62 mmol) according to the procedure described in Example 1g. Yield: 166 mg (75%). ESI-MS: 356.2 (M+H)$^+$, 286.2 (M+H-Alloc)$^+$. Rf (silica gel; dichloromethane/methanol, 17:3, v/v): 0.44.

4e. N-(N'-tert-butoxycarbonyl-N'-propoxycarbonylmethyl-D-cyclohexylalaninyl)-N-(3-(1-allyloxycarbonylamino-isoquinolin-6-oxy)-propyl))-cyclobutylamine This compound was prepared from N-(3-(1-allyloxycarbonylamino-isoquinolin-6-oxy)-propyl))-cyclobutylamine (4d, 142 mg, 0.40 mmol) and N-tert-butoxycarbonyl-N-propoxycarbonylmethyl-D-cyclohexylalanine (2g, 148 mg, 0.40 mmol) by the peptide coupling procedure described in Example 1i. Yield: 207 mg (73%). ESI-MS: 709.5 (M+H)$^+$, 653.5 (M+H—C$_4$H$_8$)$^+$, 609.6 (M+H-Boc)$^+$. Rf (silica gel; dichloromethane/methanol, 9:1, v/v): 0.61.

4f. N-(N'-propoxycarbonylmethyl-D-cyclohexylalaninyl)-N-(3-(1-amino-isoquinolin-6-oxy)-propyl))-cyclobutylamine The title compound was prepared from N-(N'-tert-butoxycarbonyl-N'-propoxycarbonylmethyl-D-cyclohexylalaninyl)-N-(3-(1-allyloxycarbonylamino-isoquinolin-6-oxy)-propyl))-cyclobutylamine (4e, 207 mg, 0.29 mmol) according to the procedure described in Example 2i for the removal of the Alloc and Boc protective groups. Purification of the residue was accomplished by the preparative HPLC procedure described in Example 1j. Desalting using 0.1 N hydrochloric acid and subsequent lyophilization yielded 36 mg (24%) of the title compound as a white fluffy solid. ESI-MS: 525.5 (M+H)$^+$, 559.9 (M+Cl). Anal. HPLC retention time (gradient Example 1j): 25.10 min (97.5% purity).

Example 5

N-(N'-propoxycarbonylmethyl-D-cyclohexylalaninyl)-N-(3-(1-amino-isoquinolin-6-oxy)-propyl))-cyclopropylamine

5a. Ethyl N-tert-butoxycarbonyl-3-cyclopropylamino-propanoate

The title compound was prepared from ethyl acrylate (1.09 ml, 10 mmol) and cyclopropylamine (0.69 ml, 10 mmol) according to Example 2a. Yield: 2.06 g (80%). ESI-MS: 258.2 (M+H)$^+$, 202.2 (M+H—C$_4$H$_8$)$^+$, 158.2 (M+H-Boc)$^+$. Rf (silica gel; ethyl acetate/heptane, 1:4, v/v): 0.38.

5b. N-tert-butoxycarbonyl-3-cyclopropylamino-propanol

This compound was prepared from N-tert-butoxycarbonyl-3-cyclopropylamino-propanoate (5a, 2.06 g, 8.0 mmol) using the procedure described in Example 2b. Yield: 1.22 g (71%). ESI-MS: 216.2 (M+H)$^+$, 160.2 (M+H—C$_4$H$_8$)$^+$. Rf (silica gel; ethyl acetate/heptane, 1:4, v/v): 0.21.

5c. N-tert-butoxycarbonyl-N-(3-(1-amino-isoquinolin-6-oxy)-propyl))-cyclopropylamine This compound was prepared from N-tert-butoxycarbonyl-3-cyclopropylamino-propanol (5b, 215 mg, 1.0 mmol) and 1-amino-6-hydroxy-isoquinoline (1e, 160 mg, 1.0 mmol) by the Mitsunobu procedure described in Example 1f. Yield: 226 mg (63%). ESI-MS: 358.1 (M+H)$^+$, 302.1 (M+H—C$_4$H$_8$)$^+$, 258.1 (M+H-Boc)$^+$. Rf (silica gel; dichloromethane/methanol, 9:1, v/v): 0.19.

5d. N-(3-(1-allyloxycarbonylamino-isoquinolin-6-oxy)-propyl))cyclopropylamine The title compound was prepared by Alloc-protection and subsequent Boc-removal of N-tert-butoxycarbonyl-3-(1-amino-isoquinolin-6-oxy)-propyl)-cyclopropylamine (5c, 226 mg, 0.63 mmol) according to the procedure described in Example 1g. Yield: 148 mg (69%). ESI-MS: 342.2 (M+H)$^+$. Rf (silica gel; dichloromethane/methanol, 17:3, v/v): 0.36.

5e. N-(N'-tert-butoxycarbonyl-N'-propoxycarbonylmethyl-D-cyclohexylalaninyl)-N-(3-(1-allyloxycarbonylamino-isoquinolin-6-oxy)-propyl))-cyclopropylamine This compound was prepared from N-(3-(1-allyloxycarbonylamino-isoquinolin-6-oxy)-propyl))-cyclopropylamine (5d, 136 mg, 0.40 mmol) and N-tert-butoxycarbonyl-N-propoxycarbonylmethyl-D-cyclohexylalanine (2g, 148 mg, 0.40 mmol) by the peptide coupling procedure described in Example 1i. Yield: 221 mg (78%). ESI-MS: 695.3 (M+H)$^+$, 639.5 (M+H—C$_4$H$_8$)$^+$, 595.3 (M+H-Boc)$^+$. Rf (silica gel; dichloromethane/methanol, 9:1, v/v): 0.49.

5f. N-(N'-propoxycarbonylmethyl-D-cyclohexylalaninyl)-N-(3-(1-amino-isoquinolin-6-oxy)-propyl))-cyclopropylamine The title compound was prepared from N-(N'-tert-butoxycarbonyl-N'-propoxycarbonylmethyl-D-cyclohexylalaninyl)-N-(3-(1-allyloxycarbonylamino-isoquinolin-6-oxy)-propyl))-cyclopropylamine (5e, 221 mg, 0.31 mmol) according to the procedure described in Example 2i for the removal of the Alloc and Boc protective groups. Purification of the residue was accomplished by the preparative HPLC procedure described in Example 1j. Desalting using 0.1 N hydrochloric acid and subsequent lyophilization yielded 87 mg (55%) of the title compound as a white fluffy solid. ESI-MS: 511.3 (M+H)$^+$, 545.9 (M+Cl). Anal. HPLC retention time (gradient Example 1j): 24.02 min (96.0% purity).

Example 6

(2S)-1-(N-propoxycarbonylmethyl-D-cyclohexylalaninyl)-2-(2-(1-amino-isoquinolin-6-oxy)-ethyl)-pyrrolidine

6a. (2S)-1-tert-butoxycarbonyl-2-(2-(1-amino-isoquinolin-6-oxy)-ethyl)-pyrrolidine This compound was prepared from N-tert-butoxycarbonyl-L-β-homoprolinol [Leyendecker, F.; Jesser, F.; Laucher, D.; *Tetrahedron Lett.* 1983, 24, 3513–3516; 590 mg, 2.75 mmol] and 1-amino-6-hydroxy-isoquinoline (1e, 320 mg, 2.0 mmol) by the Mitsunobu procedure described in Example 1f. Yield: 650 mg (91%). ESI-MS: 358.0 (M+H)$^+$. Rf (silica gel; dichloromethane/methanol, 9:1, v/v): 0.37.

6b. (2S)-2-(2-(1-allyloxycarbonylamino-isoquinolin-6-oxy)-ethyl)-pyrrolidine This compound was prepared (2S)-1-tert-butoxycarbonyl-2-(2-(1-amino-isoquinolin-6-oxy)-ethyl)-pyrrolidine (6a, 650 mg, 1.8 mmol) employing the Alloc-protection and Boc-deprotection procedure described in Example 1g. Yield: 558 mg (90%). ESI-MS: 342.2 (M+H)$^+$. Rf (silica gel; dichloromethane/methanol, 9:1, v/v): 0.22.

6c. (2S)-1-(N-propoxycarbonylmethyl-N-tert-butoxycarbonyl-D-cyclohexylalaninyl)-2-(2-(1-allyloxycarbonylamino-isoquinolin-6-oxy)-ethyl)-pyrrolidine N-Propoxycarbonylmethyl-N-tert-butoxycarbonyl-D-cyclohexylalanine (2g, 925 mg, 2.5 mmol) and (2S)-2-(2-(1-allyloxycarbonylamino-isoquinolin-6-oxy)-ethyl)-pyrrolidine (6b, 558 mg, 1.63 mmol) were reacted, using the peptide coupling protocol described in Example 1i. Yield: 590 mg (52%) of the title compound as a colourless oil. ESI-MS: 695.6 (M+H)$^+$. Rf (silica gel; dichloromethane/methanol, 9:1, v/v): 0.41.

6d. (2S)-1-(N-propoxycarbonylmethyl-D-cyclohexylalaninyl)-2-(2-(1-amino-iso-quinolin-6-oxy)-ethyl)-pyrrolidine The title compound was prepared from (2S)-1-(N-propoxycarbonylmethyl-N-tert-butoxycarbonyl-D-cyclohexylalaninyl)-2-(2-(1-allyloxycarbonylamino-isoquinolin-6-oxy)-ethyl)-pyrrolidine (6c, 590 mg, 0.85 mmol) according to the procedure described in Example 2i for the removal of the Alloc and Boc protective groups. Purification of the residue was accomplished by the preparative HPLC procedure described in Example 1j. Desalting using 0.1 N hydrochloric acid and subsequent lyophilization yielded 107 mg (25%) of the title compound as a white fluffy solid. ESI-MS: 511.6 (M+H)$^+$. Anal. HPLC retention time (gradient Example 1j): 42.96 min (96.4% purity).

Example 7

1-(N-propoxycarbonylmethyl-D-cyclohexylalaninyl)-2-(2-(1-amino-isoquinolin-6-oxy)-ethyl)-piperidine

7a. 1-(N-propoxycarbonylmethyl-N-tert-butoxycarbonyl-D-cyclohexylalaninyl)-2-(2-(1-allyloxycarbonylamino-isoquinolin-6-oxy)-ethyl)-piperidine 2-(2-(1-Allyloxycarbonylamino-isoquinolin-6-oxy)-ethyl)-piperidine (1g, 330 mg, 0.75 mmol) and N-propoxycarbonylmethyl-N-tert-butoxycarbonyl-D-cyclohexylalanine (2g, 273 mg, 0.75 mmol) were condensed, using the peptide coupling protocol described in Example 1i, affording 239 mg (45%) of the title compound as a colourless oil. ESI-MS: 709.7 (M+H)$^+$. Rf (silica gel; dichloromethane/methanol, 9:1, v/v): 0.56.

7b. 1-(N-propoxycarbonylmethyl-D-cyclohexylalaninyl)-2-(2-(1-amino-isoquinolin-6-oxy)-ethyl)-piperidine The title compound was prepared by Alloc-deprotection and subsequent Boc-removal of 1-(N- propoxycarbonylmethyl-N-tert-butoxycarbonyl-D-cyclohexylalaninyl)-2-(2-(1-allyloxycarbonylamino-isoquinolin-6-oxy)-ethyl)-piperidine (7a, 239 mg, 0.34 mmol) according to the procedure described in Example 1j. Purification of the residue was effected by the preparative HPLC procedure described in Example 1j. Desalting using 0.1 N hydrochloric acid and subsequent lyophilization yielded 87 mg (49%) of the title compound (2 diastereomers) as a white fluffy solid. ESI-MS: 525.4 (M+H)$^+$. Anal. HPLC retention time (gradient Example 1j): 25.88 min (32.4%) and 27.52 min (66.6%).

Example 8

1-(N-cyclooctyl-γ-tert-butyl-L-glutamyl)-2-(2-(1-amino-isoquinolin-6-oxy)-ethyl)-piperidine

8a. N-cyclooctyl-γ-tert-butyl-L-glutamic acid

To a stirred suspension of γ-tert-butyl-L-glutamic acid (4.06 g, 20.0 mmol) and cyclooctanone (3.15 g, 25 mmol) in N,N-dimethylformamide/acetic acid (99:1, v/v, 50 mL) was added sodium triacetoxyborohydride (6.36 g, 30.0 mmol) in small portions and the mixture was stirred overnight. After evaporation of the solvent, the residue was dissolved in water (50 mL). The pH was adjusted to 9 with 2 N sodium hydroxide solution, followed by extraction with diethylether (50 mL). Subsequently, the pH of the aqueous layer was carefully adjusted to 2.5 using 1.0 N hydrochloric acid. Extraction with dichloromethane afforded an organic layer, which was dried (magnesium sulphate) and concentrated under reduced pressure, yielding 4.82 g (77%) of the title compound as a white solid. ESI-MS: 314.2 (M+H)$^+$, 336.2 (M+Na)$^+$. Rf (silica gel; ethyl acetate/pyridine/acetic acid/water 63:20:6:11, v/v): 0.80.

8b. 1-(N-cyclooctyl-γ-tert-butyl-L-glutamyl)-2-(2-(1-allyloxycarbonylamino-isoquinolin-6-oxy)-ethyl)-piperidine N-Cyclooctyl-γ-tert-butyl-L-glutamic acid (8a, 344 mg, 1.1 mmol) and 2-(2-(1-allyloxycarbonylamino-isoquinolin-6-oxy)-ethyl)-piperidine (1g, 391 mg, 1.1 mmol) were coupled, using the methodology described in Example 1i, providing 380 mg (58%) of the title compound as a colourless oil. ESI-MS: 651.3 (M+H)$^+$. Rf (silica gel; dichloromethane/methanol, 9:1, v/v): 0.23.

8c. 1-(N-cyclooctyl-γ-tert-butyl-L-glutamyl)-2-(2-(1-amino-isoquinolin-6-oxy)-ethyl)-piperidine This compound was prepared from 1-(N-cyclooctyl-γ-tert-butyl-L-glutamyl)-2-(2-(1-allyloxyamino-isoquinolin-6-oxy)-ethyl)-piperidine (8b, 380 mg, 0.58 mmol) using the Alloc-removal and purification procedure as described in Example 1j. Yield: 81 mg (25%, 2 diastereoisomers at piperidine C-2). ESI-MS: 567.4 (M+H)$^+$. Anal. HPLC retention time (gradient Example 1j): 26.20 min (47.2% purity) and 27.07 min (52.0% purity).

Example 9

1-(N-cyclopentylaminocarbonylmethyl-D-cyclohexylalaninyl)-2-(2-(1-amino-isoquinolin-6-oxy)-ethyl)-piperidine

9a. N-Allyloxycarbonyl-N-tert-butoxycarbonylmethyl-D-cyclohexylalanine

To a stirred solution of N-tert-butoxycarbonylmethyl-D-cyclohexylalanine [Hamada, Y.; Shibata, M.; Sugiura, T.; Kato, S.; Shioiri, T.; *J. Org. Chem.* 1987, 52, 1252–1255; 2.85 g, 10 mmol] in 1,4-dioxane (50 mL) were sequentially added saturated aqueous sodium hydrogencarbonate (25 mL) and allyl chloroformate (1.17 ml, 11 mmol). After stirring for 3 d, the reaction mixture was carefully acidified (pH=3) using 1 N hydrochloric acid and subsequently extracted with dichloromethane. Drying over magnesium sulphate and concentration under reduced pressure furnished the target compound as a white solid (2.41 g, 65%). ESI-MS: 370.4 (M+H)$^+$, 314.4 (M+H—C$_4$H$_8$)$^+$, 230.3 (M+H—C$_4$H$_8$-Alloc)$^+$. Rf (silica gel; ethyl acetate/pyridine/acetic acid/water, 63/20/10/7, v/v): 0.69.

9b. 1-(N-Allyloxycarbonyl-N-tert-butoxycarbonylmethyl-D-cyclohexylalaninyl)-2-(2-(1-allyloxycarbonylamino-isoquinolin-6-oxy)-ethyl)-piperidine 2-(1H-benzotriazol-1-yl)-1,1,3,3-tetramethyluronium tetrafluoroborate (TBTU, 616 mg, 1.9 mmol) was added to a stirred solution of 2-(2-(1-allyloxycarbonylamino-isoquinolin-6-oxy)-ethyl)-piperidine (1g, 676 mg, 1.9 mmol) and N-allyloxycarbonyl-N-tert-butoxycarbonylmethyl-D-cyclohexylalanine (9a, 709 mg, 1.9 mmol) in N,N-dimethylformamide (15 mL) at 0° C. The pH was adjusted to 8 with N,N-diisopropylethylamine. After stirring overnight at room temperature, the reaction mixture was concentrated in vacuo. The residue was diluted with ethyl acetate (100 mL), washed with 5% (w/w) aqueous sodium hydrogencarbonate (2×50 mL) and brine (50 mL), dried (magnesium sulphate) and concentrated under reduced pressure. Purification of the residue was effected by silica gel chromatography (eluent: 33–50% ethyl acetate in heptane), yielding 825 mg (57%) of the title compound as a white foam. ESI-MS: 707.4 (M+H)$^+$. Rf (silica gel; ethyl acetate/pyridine/acetic acid/water, 232/31/18/7, v/v): 0.91.

9c. 1-(N-allyloxycarbonyl-N-carboxymethyl-D-cyclohexylalaninyl)-2-(2-(1-allyloxy-carbonylamino-isoquinolin-6-oxy)-ethyl)-piperidine A solution of 1-(N-allyloxycarbonyl-N-tert-butoxycarbonylmethyl-D-cyclohexyl-alaninyl)-2-(2-(1-allyloxycarbonylamino-isoquinolin-6-oxy)-ethyl)-piperidine (9b, 825 mg, 1.3 mmol) in trifluoroacetic acid/dichloromethane (2/3, v/v) was stirred for 5 h at room temperature. The reaction mixture was concentrated in vacuo yielding 0.76 g (100%) of a brownish solid. ESI-MS: 651.4 (M+H)$^+$, 649.4 (M−H)$^+$, Rf (silica gel; ethyl acetate/pyridine/acetic acid/water, 232/31/18/7, v/v): 0.31.

9d. 1-(N-allyloxycarbonyl-N-cyclopentylaminocarbonylmethyl-D-cyclohexylalaninyl)-2-(2-(1-allyloxycarbonylamino-isoquinolin-6-oxy)-ethyl)-piperidine 1-(N-Allyloxycarbonyl-N-carboxylmethyl-D-cyclohexylalaninyl)-2-(2-(1-allyloxycarbonylamino-isoquinolin-6-oxy)-ethyl)-piperidine (9c, 189 mg, 0.29 mmol) and cyclopentylamine (40.3 μl, 0.41 mmol) were condensed using the procedure described in Example 9b, yielding 187 mg (90%) of the title compound. ESI-MS: 718.4 (M+H)$^+$, 716.4 (M−H)$^-$. Rf (silica gel; dichloromethane/methanol, 95/5, v/v): 0.72.

9e. 1-(N-cyclopentylaminocarbonylmethyl-D-cyclohexylalaninyl)-2-(2-(1-amino-isoquinolin-6-oxy)-ethyl)-piperidine The Alloc protective groups in 1-(N-allyloxycarbonyl-N-cyclopentylamino-carbonylmethyl-D-cyclohexylalaninyl)-

2-(2-(1-allyloxycarbonylamino-isoquinolin-6-oxy)-ethyl)-piperidine (9d, 187 mg, 0.26 mmol) were removed according to the procedure described in Example 1j (10 mol % Pd, 10 eq. morpholine). Purification of the residue was accomplished by the preparative HPLC procedure described in Example 1j. Desalting using 0.1 N hydrochloric acid and subsequent lyophilization yielded 102 mg (66%) of the tide compound (2 diastereomers) as a white fluffy solid. ESI-MS: 550.4 (M+H)$^+$, 272 ($C_{16}H_{22}N_3O$)$^+$, 251 ($C_{15}H_{27}N_2O$)$^+$, 548.4 (M–H)$^-$, 584 (M+Cl)$^-$. Anal. HPLC retention time (gradient Example 1j): 31.19 min (44.4%) and 33.31 min (55.6%).

Example 10

1-(N-anilinocarbonylmethyl-D-cyclohexylalaninyl)-2-(2-(1-amino-isoquinolin-6-oxy)-ethyl)-piperidine 10a. 1-(N-allyloxycarbonyl-N-anilinocarbonylmethyl-D-cyclohexylalaninyl)-2-(2-(1-allyloxycarbonylamino-isoquinolin-6-oxy)-ethyl)-piperidine Using the procedure described in Example 9b 1-(N-allyloxycarbonyl-N-hydroxycarbonylmethyl-D-cyclohexylalaninyl)-2-(2-(1-allyloxycarbonylamino-isoquinolin-6-oxy)-ethyl)-piperidine (9c, 189 mg, 0.29 mmol) and aniline (38 µl, 0.41 mmol) were coupled. Yield: 206 mg (98%). ESI-MS: 726.4 (M+H)$^+$. Rf (silica gel; dichloromethane/methanol, 95/5, v/v): 0.73.

10b. 1-(N-anilinocarbonylmethyl-D-cyclohexylalaninyl)-2-(2-(1-amino-isoquinolin-6-oxy)-ethyl)-piperidine The Alloc protective groups in 1-(N-allyloxycarbonyl-N-anilinocarbonylmethyl-D-cyclohexylalaninyl)-2-(2-(1-allyloxycarbonylamino-isoquinolin-6-oxy)-ethyl)-piperidine (10a, 206 mg, 0.28 mmol) were removed according to the procedure described in Example 1j (10 mol %. Pd, 10 eq. morpholine). Purification of the residue was accomplished by the preparative HPLC procedure described in Example 1j. Desalting using 0.1 N hydrochloric acid and subsequent lyophilization afforded 80 mg (51%) of the title compound (2 diastereomers) as a white fluffy solid. ESI-MS: 558.0 (M+H)$^+$, 580.1 (M+Na)$^+$, 272.2 ($C_{16}H_{22}N_3O$)$^+$, 259.3 ($C_{16}H_{23}N2O$)$^{30}$, 556.0 (M–H)$^-$, 592.3 (M+Cl)$^-$, Rf (silica gel; dichloromethane/methanol, 95/5, v/v): 0.32. Anal. HPLC retention time (gradient Example 1j): 32.76 min (43.5%) and 34.52 min (56.5%).

Example 11

1-(N-cyclohexyl-D-cyclohexylalanine)-2-(2-(1-amino-isoquinolin-6-oxy)-ethyl)-piperidine 11a. N-cyclohexyl-D-cyclohexylalanine Cyclohexanone (1.55 ml, 15 mmol) was added to a stirred suspension of D-cyclohexylalanine.HCl salt (2.08 g, 10 mmol) in N,N-dimethylformamide (10 mL), containing 0.1 mL of acetic acid. Subsequently, sodium triacetoxyborohydride (3.18 g, 15 mmol) was added and the reaction mixture was stirred overnight. After 17 h, the clear solution was concentrated under reduced pressure and suspended in water (15 mL). After acidification (1 N hydrochloric acid) of the heterogeneous mixture to pH=3.0, dichloromethane (150 mL) was added and the mixture was stirred mechanically for 30 min. The organic layer was dried (magnesium sulphate) and concentrated under reduced pressure, providing 1.57 g (63%) of the title compound as a white solid. ESI-MS: 254.2 (M+H)$^+$, 252.1 (M–H)$^-$. Rf (silica gel; dichloromethane/methanol, 8:2, v/v): 0.29.

11b. 1-(N-cyclohexyl-D-cyclohexylalaninyl)-2-(2-(1-allyloxycarbonylamino-isoquinolin-6-oxy)-ethyl)-piperidine This compound was prepared from N-cyclohexyl-D-cyclohexylalanine (11a, 127 mg, 0.50 mmol) and 2-(2-(1-allyloxycarbonylamino)-isoquinolin-6-oxy)-ethyl)-piperidine (1 g, 178 mg, 0.50 mmol) by the peptide coupling procedure described in Example 1i. Yield: 224 mg (76%). ESI-MS: 591.4 (M+H)$^-$, 589.4 (M–H)$^-$, 507.3 (M+H-Alloc)$^+$. Rf (silica gel; dichloromethane/methanol, 9:1, v/v): 0.69/0.72 (2 diastereomers at piperidine C-2).

11c. 1-(N-cyclohexyl-D-cyclohexylalaninyl)-2-(2-(1-amino-isoquinolin-6-oxy)-ethyl)-piperidine This compound was prepared from 1-(N-cyclohexyl-D-cyclohexylalaninyl)-2-(2-(1-allyloxycarbonylamino-isoquinolin-6-oxy)-ethyl)-piperidine (11b, 224 mg, 0.38 mmol) following the procedure described in Example 1j for the removal of the Alloc protective group. Purification of the residue was effected by the preparative HPLC procedure described in Example 1j. Desalting using 0.1 N hydrochloric acid and subsequent lyophilization yielded 102 mg (53%) of the title compound as a white fluffy solid (2 diastereomers at piperidine C-2). ESI-MS: 507.3 (M+H)$^+$, 623.4 (M+Cl). Yield: 224 mg (76%). ESI-MS: 507.3 (M+H)$^+$. Anal. HPLC retention time (gradient Example 1j): 30.94 min (41.2%); 32.20 min (53.4%).

Example 12

N-(N'-iso-propoxycarbonylmethyl-D-diphenylalaninyl)-N-(3-(1-amino-isoquinolin-6-oxy)-propyl))-cyclohexylamine According to the procedures described in the preceding examples N-(N'-iso-propoxycarbonylmethyl-D-diphenylalaninyl)-N-(3-(1-amino-isoquinolin-6-oxy)-propyl))-cyclohexylamine was prepared. This compound (1.11 g) was with 1 mL of dichloromethane and 9 mL of trifluoroacetic acid. After stirring at room temperature for 16 h the reaction mixture was concentrated, treated with toluene, and concentrated again. The residue was treated with a mixture of t-butanol and water, washed with ether and concentrated. Addition of ethanol to the residue, filtration and removal of the ethanol from the filtrate gave 0.72 g of N-(N'-hydroxycarbonylmethyl-D-diphenylalaninyl)-N-(3-(1-amino-isoquinolin-6-oxy)-propyl))-cyclohexylamine. To 0.34 g of this compound were added 10 mL of 2-propanol and 0.16 mL of thionyl chloride. After stirring for 18 h at 60° C. the reaction mixture and concentrated. The residue was subjected twice to column chromatography (silica gel, first column: dichloromethane/methanol=9/1 (v/v); second column: toluene/ethanol=98/2 gradient to 95/5 (v/v). The crude product was triturated with ether to yield 45 mg of the title compound. ESI-MS: 595 (M+H)$^+$, 629 (M+Cl)$^-$. Anal. HPLC (Supelcosil LC-18-DB 5 um, 250*2.1 mm): Mob. phase: A=0.5 M $NaH_2PO_4+H_3PO_4$ pH 2.1; B=$H_2O$; C=$CH_3CN/H_2O$ (3:2, v/v).

| Gradient: | Time (min) | % A | % B | % C |
|---|---|---|---|---|
| | 0 | 20 | 60 | 20 |
| | 40 | 20 | 0 | 80 |

Retention time: 34.9 min and 37.4 min.

Example 13

N-(N'-cyclopentylaminocarbonylmethyl-D-diphenylalaninyl)-N-(3-(1-amino-isoquinolin-6-oxy)-propyl))-cyclohexylamine The title compound (56 mg) was prepared according to the procedures described in the preceding examples from N-(N'-hydroxycarbonylmethyl-D-diphenylalaninyl)-N-(3-(1-amino-isoquinolin-6-oxy)-propyl))-cyclohexylamine (380 mg). ESI-MS: 620 (M+H)$^+$, 654 (M+Cl)$^-$. Anal. HPLC (gradient Example 12) retention time: 37.2 min.

Example 14a–f

Preparation of the following compounds according to the procedures described in the preceding examples:

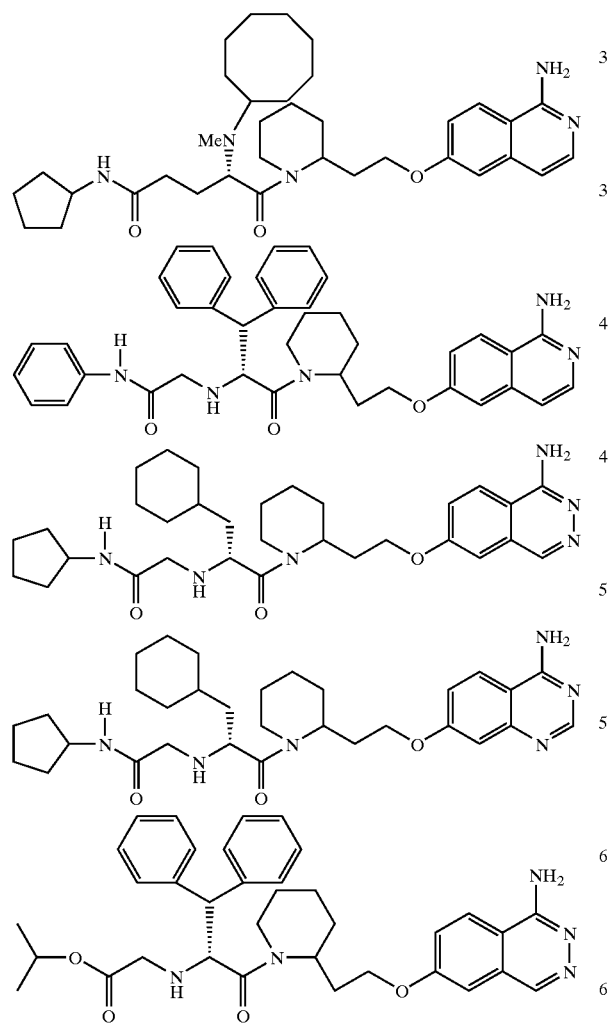

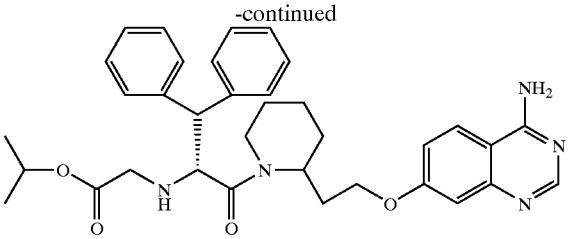

Example 15

The biological activities of the compounds of the present invention were determined by the following test method.

Anti-thrombin Assay

Thrombin (Factor IIa) is a factor in the coagulation cascade. The anti-thrombin activity of compounds of the present invention was assessed by measuring spectrophotometrically the rate of hydrolysis of the chromogenic substrate s-2238 exterted by thrombin. This assay for antithrombin activity in a buffer system was used to assess the $IC_{50}$-value of a test compound.

Test medium: Tromethamine-NaCl-polyethylene glycol 6000 (TNP) buffer

Reference compound: 12581 (Kabi)

Vehicle: TNP buffer. Solubilisation can be assisted with dimethylsulphoxide, methanol, ethanol, acetonitrile or tert.-butyl alcohol which are without adverse effects in concentrations up to 2.5% in the final reaction mixture.

Technique Reagents*

1. Tromethamine-NaCl (TN) buffer Composition of the buffer:

| | |
|---|---|
| Tromethamine (Tris) | 6.057 g (50 mmol) |
| NaCl | 5.844 g (100 mmol) |
| Water to | 1 l |

The pH of the solution is adjusted to 7.4 at 37° C. with HCl (10 mmol.l$^{-1}$).

2. TNP buffer Polyethylene glycol 6000 is dissolved in TN buffer to give a concentration of 3 g.l$^{-1}$.
3. S-2238 solution One vial S-2238 (25 mg; Kabi Diagnostica, Sweden) is dissolved in 20 ml TN buffer to give a concentration of 1.25 mg.ml$^{-1}$ (2 mmol.l$^{-1}$).
4. Thrombin solution Human thrombin (16 000 nKat.vial$^{-1}$; Centraal Laboratorium voor Bloedtransfusie, Amsterdam, The Netherlands) is dissolved in TNP buffer to give a stock solution of 835 nKat.ml$^{-1}$. Immediately before use this solution is diluted with TNP buffer to give a concentration of 3.34 nKat.ml$^{-1}$.

All ingredients used are of analytical grade

For aqueous solutions ultrapure water (Milli-Q quality) is used.

Preparation of test and reference compound solutions

The test and reference compounds are dissolved in Milli-Q water to give stock concentrations of 10$^{-2}$ mol.l$^{-1}$. Each concentration is stepwise diluted with the vehicle to give concentrations of 10$^{-3}$, 10$^{-4}$ and 10$^{-5}$ mol.l$^{-1}$. The dilutions, including the stock solution, are used in the assay (final concentrations in the reaction mixture: 3·10$^{-3}$; 10$^{-3}$; 3·10$^{-4}$; 10$^{-4}$; 3·10$^{-5}$; 10$^{-5}$; 3·10$^{-6}$ and 10$^{-6}$ mol.l$^{-1}$, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories). All data are collected in an IBM personal computer using LOTUS-MEASURE. For each compound concentration (expressed in mol.l$^{-1}$ reaction mixture) and for the blank the absorbance is plotted versus the reaction time in min.

Evaluation of responses: For each final concentration the maximum absorbance was calculated from the assay plot. The $IC_{50}$-value (final concentration, expressed in $\mu$mol.l$^{-1}$, causing 50% inhibition of the maximum absorbance of the blank) was calculated using the logit transformation analysis according to Hafner et al. (Arzneim.-Forsch./Drug Res. 1977; 27(II): 1871–3).

| Antithrombin activity: | |
| --- | --- |
| Example | $IC_{50}$ ($\mu$mol · l$^{-1}$) |
| 1 | 0.41 |
| 8 | 0.61 |
| 9 | 0.32 |
| 10 | 1.35 |
| 11 | 0.5 |

What is claimed is:

1. A serine protease inhibitor having the formula (I),

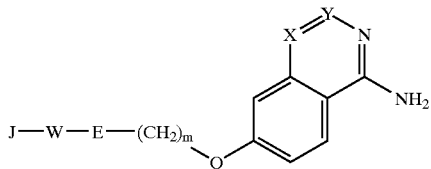

in which

J is H, $R^1$, $R^1$—O—C(O)—, $R^1$—C(O)—, $R^1$—SO$_2$—, $R^3$OOC—(CHR$^2$)$_p$—, (R$^{2a}$,R$^{2b}$)N—CO—(CHR$^2$)$_p$— or Het—CO—(CHR$^2$)$_p$—;

Z is an amino-acid of the formula —NH—CHR$^1$—C(O)—, —NR$^4$—CH((CH$_2$)$_q$C(O)OR$^1$)—C(O)—, —NR$^4$—CH((CH$_2$)$_q$C(O)N(R$^{2a}$,R$^{2b}$))—C(O)—, —NR$^4$—CH((CH$_2$)$_q$C(O)Het)-C(O)—, D-1-Tiq, D-3-Tiq, D-Atc, Aic, D-1-Piq, D-3-Piq, glutamyl or a (C$_1$-C$_6$) alkylester thereof;

E is —NR$^2$—CH$_2$— or the fragment

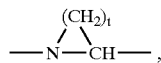

which is unsubstituted or substituted with (1–6C)alkyl, (1–6C)alkoxy or benzyloxy;

$R^1$ is selected form (1–12C)alkyl, (2–12C)alkenyl, (2–12C)alkynyl, (3–12C)cycloalkyl and (3–12C)cycloalkyl(1–6C)alkylene, which groups are unsubstituted or substituted with (3–12C)cycloalkyl, (1–6C) alkoxy, oxo, OH, CF$_3$ or halogen, and from (6–14C) aryl, (7–15C)aralkyl, (8–16C)aralkenyl and (14–20C) (bisaryl)alkyl, wherein the aryl groups are unsubstituted or substituted with (1–6C)alkyl, (3–12C) cycloalkyl, (1–6C)alkoxy, OH, CF$_3$ or halogen;

$R^2$, $R^{2a}$ and $R^{2b}$ are each independently selected from H, (1–8C)alkyl, (3–8C)alkenyl, (3–8C)alkynyl, (3–8C) cycloalkyl and (3–6C)cycloalkyl(1–4C)alkylene, which are unsubstituted or substituted with (3–6C) cycloalkyl, (1–6C)alkoxy, CF$_3$ or halogen, and from (6–14C)aryl and (7–15C)aralkyl, wherein the aryl groups are unsubstituted or substituted with (1–6C) alkyl, (3–6C)cycloalkyl, (1–6C)alkoxy, CF$_3$ or halogen;

$R^3$ is the same as $R^2$ or is Het-(1–6C)alkyl;

$R^4$ is H or (1–3C)alkyl;

X and Y are CH or N, with the proviso that they are not both N;

Het is a 4-, 5- or 6-membered heterocycle containing one or more heteroatoms selected from O, N and S m is 1 or 2;

p is 1, 2 or 3;

q is 1, 2 or 3;

t is 2, 3 or 4;

Tiq is 1,2,3,4-tetrahydroisoquinoline-3-carboxylic acid;

Atc is 2-aminotetraline-2-carboxylic acid;

Aic is 2-aminoindan-2-carboxylic acid; and

Piq is 1-perhydroisoquinolyl carboxylic acid;

or a pharmaceutically acceptable addition salt or solvate thereof.

2. The serine protease inhibitor according to claim 1, wherein m is 2; X is CH and Y is CH.

3. The serine protease inhibitor according to claim 2, wherein

J is H, $R^1R^1$—SO$_2$—, $R^3$OOC—(CHR$^2$)$_p$—, (R$^{2a}$,R$^{2b}$) N—CO—(CHR$^2$)$_p$— or Het-CO(CHR$^2$)p—;

Z is an amino-acid of the formula —NH—CHR$^3$—C (O)—, —NR$^4$—CH((CH$_2$)$_q$C(O)OR$^1$)—C(O)—, —NR$^4$—CH((CH$_2$)$_q$C(O)](R$^{2a}$,R$^{2b}$))—C(O)—;

E is —N(3–6C)cycloalkyl-CH$_2$— or the fragment

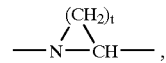

which is unsubstituted or substituted with (1–6C)alkyl or 1–6C)alkoxy;

$R^1$ is selected from (1–12C)alkyl, (3–12C)cycloalkyl and (3–12C)cycloalkyl(1–6C)alkylene, which groups are unsubstituted or substituted with (3–12C)cycloalkyl, (1–6C alkoxy or oxo, and from (6–14C)aryl, (7–15C) aralkyl and (14–20C)(bisaryl)alkyl, wherein the aryl groups are unsubstituted or substituted with (1–6C) alkyl, (3–12C)cycloalkyl, (1–6C)alkoxy, OH, CF$_3$ or halogen;

$R^2$ is H;

$R^{2a}$ and $R^{2b}$ are each independently selected from H, (1–8C)alkyl, (3–8C)cycloalkyl and (3–6C)cycloalkyl (1–4C)alkylene, which are unsubstituted or substituted with (3–6C)cycloalkyl or (1–6C)alkoxy and from (6–14C)aryl and (7–15C)aralkyl, wherein the aryl groups are unsubstituted or substituted with (1–6C) alkyl, (3–6C)cycloalkyl, (1–6C)alkoxy, CF$_3$ or halogen;

R³ is selected from H, (1–8C)alkyl, (3–8C)cycloalkyl and (3–6C)cycloalkyl(1–4C)alkylene, which are unsubstituted or substituted with (3–6C)cycloalkyl or (1–6C)alkoxy, and from (7–15C)aralkyl, wherein the aryl groups are unsubstituted or substituted with (1–6C)alkyl, (3–6C)cycloalkyl, (1–6C)alkoxy, CF₃ or halogen and from Het-(1–6C)alkyl;

p is 1;

q is 2;

t is 3 or 4.

4. The serine protease inhibitor according to claim 3, wherein

Z is an amino-acid of the formula —NH—CHR¹—C(O)— or glutamyl or an (1–6C)alkylester thereof;

R¹ is selected from (3–12C)cycloalkyl and (3–12C)cycloalkyl(1–6C)alkylene, which groups are unsubstituted or substituted with (3–12C)cycloalkyl or (1–6C)alkoxy, and from (6–14C)aryl, (7–15C)aralkyl and (14–20C)(bisaryl)alkyl, wherein the aryl groups are unsubstituted or substituted with (1–6C)alkyl, (3–12C)cycloalkyl, (1–6C)alkoxy or halogen; and R³ is selected from (1–8C)alkyl and (3–8C)cycloalkyl, which are unsubstituted or substituted with (3–6C)cycloalkyl or (1–6C)alkoxy, and from (7–15C)aralkyl, wherein the aryl groups are unsubstituted or substituted with (1–6C)alkyl, (3–6C)cycloalkyl, (1–6C)alkoxy, CF₃ or halogen and from Het-(1–6C)alkyl.

5. The serine protease inhibitor according to claim 4, wherein

J is —CH₂COO(1–6C)alkyl, (3–8C)cycloalkyl, —SO₂-10-camphor, —CH₂CONHphenyl or —CH₂CONH(3–8C)cycloalkyl Z is D-cyclohexylalaninyl, D-phenylalaninyl, D-diphenylalaninyl or glutamyl, or an (1–6C)alkylester thereof; and;

E is the fragment

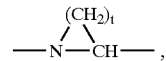

wherein t is 3 or 4.

6. A pharmaceutical composition comprising the serine protease inhibitor of claim 1 and at least one pharmaceutically suitable auxiliary.

7. A method of inhibiting coagulation by serine proteases in the blood coagulation cascade in a mammal, comprising:
administering to the mammal an effective amount of a serine protease inhibitor according to claim 1.

8. A method for treating a thrombin-mediated and thrombin-associated disease in a mammal, comprising:
administering an effective amount of the serine protease inhibitor according to claim 1.

9. The method according to claim 8, wherein the thrombin-mediated and thrombin-associated diseases are selected from the group consisting of deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, and myocardial infarction.

10. An anticoagulant composition, comprising: the serine protease inhibitor according to claim 1, and a pharmaceutically acceptable carrier or excipient.

* * * * *